United States Patent [19]
Rydell

[11] Patent Number: 5,356,408
[45] Date of Patent: Oct. 18, 1994

[54] BIPOLAR ELECTROSURGICAL SCISSORS HAVING NONLINEAR BLADES

[75] Inventor: Mark A. Rydell, Golden Valley, Minn.

[73] Assignee: Everest Medical Corporation, Minneapolis, Minn.

[21] Appl. No.: 92,076

[22] Filed: Jul. 16, 1993

[51] Int. Cl.$^5$ .............................................. A61D 17/39
[52] U.S. Cl. ........................................ 606/48; 606/50; 606/174
[58] Field of Search ................. 606/48, 51, 45, 46, 606/49, 50, 52, 159, 170, 174, 205

[56] References Cited

U.S. PATENT DOCUMENTS

| | | |
|---|---|---|
| 3,651,811 | 3/1972 | Hildebrandt et al. ............... 606/51 |
| 4,985,030 | 1/1991 | Melzer et al. ........................ 606/51 |
| 5,147,357 | 9/1992 | Rose et al. ........................... 606/51 |
| 5,209,747 | 5/1993 | Knoepfler ............................ 606/52 |
| 5,281,220 | 1/1994 | Blake, III ........................... 606/51 |

FOREIGN PATENT DOCUMENTS 0518230A 5/1992 European Pat. Off. .

OTHER PUBLICATIONS

"Two New Laparoscopic Instruments: Bipolar Sterilizing Forceps and Uterine Manipulator" by Stephen Corson, Medical Instrumentation, vol. 11, No. 1.
Cameron-Miller product brochure for Model 80-7527.

Primary Examiner—Lee S. Cohen
Assistant Examiner—Brian M. Green
Attorney, Agent, or Firm—Haugen and Nikolai

[57] ABSTRACT

A bipolar electrosurgical scissors instrument comprising a proximal portion having a proximal linear axis and a distal blade portion having blade members with a nonlinear axis in relation to the proximal linear axis. The blade members each comprise an electrically conductive outer surface and an electrically nonconductive inner surface, with the inner surface comprising a ceramic layer having a honed cutting edge. At least one, and preferably both, of the blade members can pivot in relation to each other. Pivoting of the blade members causes the honed cutting edge of the first blade member to wipe the honed cutting edge of the second blade member to thereby cause separation of tissue therebetween. The blade members in one preferred embodiment are curved in relation to the proximal linear axis, while the blade members in a second preferred embodiment are angled in relation to the proximal linear axis. In this manner the proximal linear-axis portion of the scissors instrument does not obscure the visualization of the blade members during performance of a surgical procedure.

12 Claims, 2 Drawing Sheets

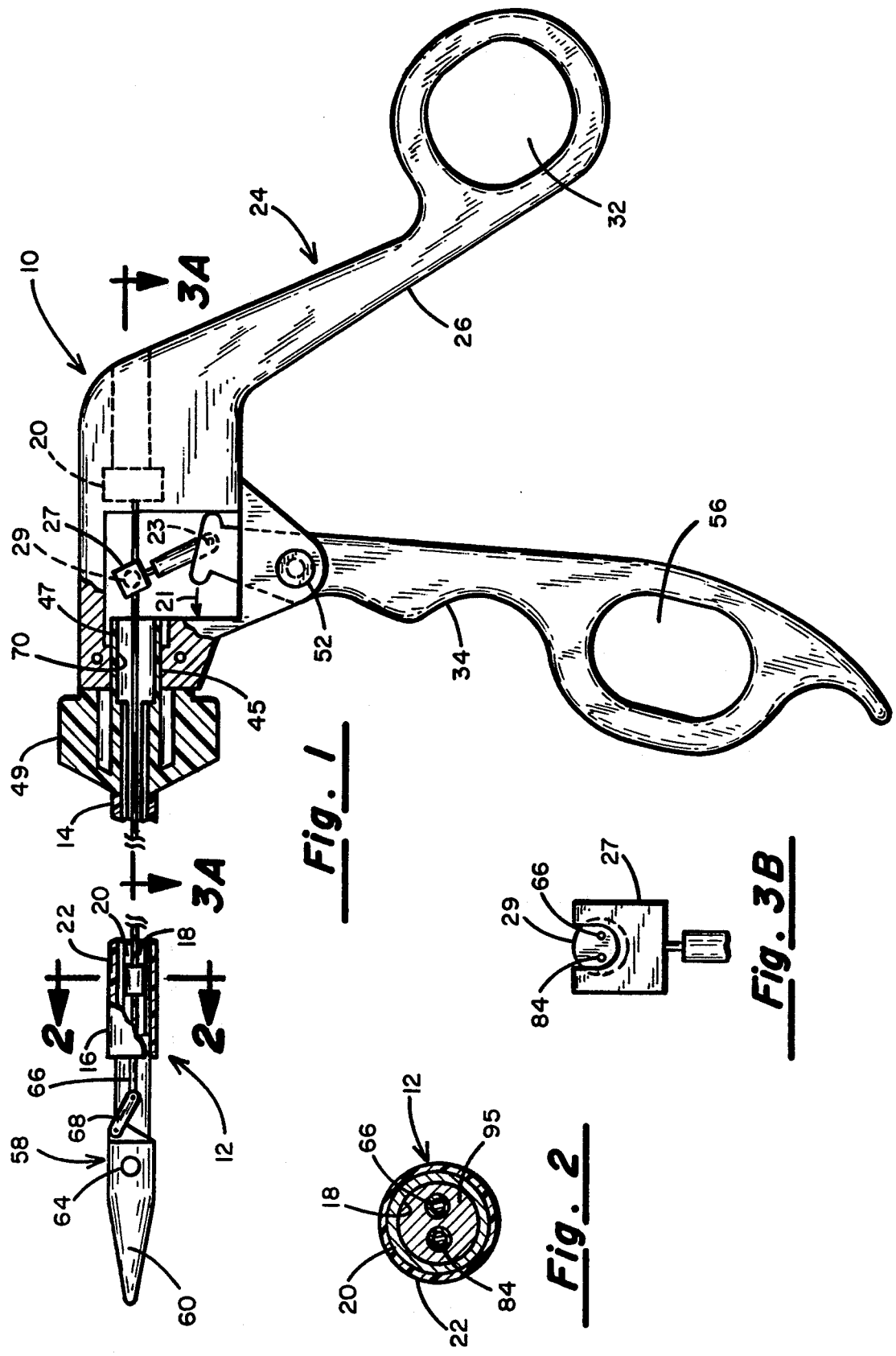

BIPOLAR ELECTROSURGICAL SCISSORS HAVING NONLINEAR BLADES

BACKGROUND OF THE INVENTION

I. Field of the Invention

This invention relates generally to surgical scissors, and in particular to a bipolar scissors instrument wherein the axis of distal blade members thereof is nonlinear in relation to a linear axis of the instrument proximal to the blade members.

II. Discussion of the Prior Art

Electrocauterization is a process whereby blood vessels (commonly called "bleeders") in tissue or alone which are cut during a surgical procedure are sealed closed by applying electrical energy at the site to, essentially, fuse by heat the vessel opening. In order to provide electrical energy at the site of bleeding, an instrument capable of conducting electricity must be placed at that site. The conductive instrument may be comprised of one electrode (monopolar) which cooperates with a remote conductive body plate electrode, or the instrument may be comprised of two closely spaced electrodes (bipolar). Current passing from one electrode to the other produces the heat sufficient to seal blood vessels or to coagulate blood and other fluids. A bipolar instrument is generally preferred by a physician since current travel is over a short distance. A monopolar instrument usually requires electric current to travel a relatively long distance to the body plate electrode, with current directability and effect being unpredictable and possibly harmful to a patient.

Surgical scissors are known in the art. Those available for use in endoscopically performed surgeries or other similar scope procedures are of a size to fit distally through the scope while having operating handles proximally of the scope. Generally, the scissors include a proximal scissors type handle, a central hollow tube through which a linkage from the handle passes, and a distal blade pair to which the linkage connects. Copending and commonly assigned patent application Ser. No. 08/013,869, filed Feb. 5, 1993, and entitled "BIPOLAR ELECTRICAL SURGICAL SCISSORS," teaches a bipolar scissors instrument wherein both of the blades thereof pivot in relation to each other. A ceramic layer is present on each of the respective inner surfaces of each blade member, and insulation means at strategic sites throughout the instrument maintain bipolar capability for the separate blade members. The central hollow tube described above and the distal blade pair lie in a single linear axis. Such a single axis can create a visibility problem in some circumstances since a view of the blade members may be obstructed by the immediately-proximal portion of the instrument because it is in the same linear axis as that of the blade members.

It is therefore a primary object of the present invention to provide a bipolar electrosurgical scissors instrument whose blade members are in a nonlinear axis in relation to a proximal linear axis of the instrument.

It is a further object of the present invention to provide a bipolar electrical surgical scissors instrument or in the blade members are arcuate or angled.

These and other objects of the present invention will become apparent in the description of the invention which follows.

SUMMARY OF THE INVENTION

The present invention is a bipolar electrosurgical scissors instrument comprising a proximal portion having a proximal linear axis and a distal blade portion having blade members with a nonlinear axis in relation to the proximal linear axis. The blade members each comprise an electrically conductive outer surface and an electrically nonconductive inner surface, with the inner surface comprising a ceramic layer having a honed cutting edge. At least one, and preferably both, of the blade members can pivot in relation to each other. Pivoting of the blade members causes the honed cutting edge of the first blade member to wipe the honed cutting edge of the second blade member to thereby cause separation of tissue therebetween. The blade members in one preferred embodiment are curved in relation to the proximal linear axis, while the blade members in a second preferred embodiment are angled in relation to the proximal linear axis. In this manner the proximal linear-axis portion of the scissors instrument does not obscure the visualization of the blade members during performance of a surgical procedure.

BRIEF DESCRIPTION OF THE DRAWINGS

FIG. 1 is a side elevation view of a bipolar electrosurgical scissors instrument having two movable curved blade members, the drawing being partially sectioned to illustrate the working elements of the embodiment;

FIG. 2 is a cross section view along line 2—2 of FIG. 1;

FIG. 3B is a front elevation view of a portion of a coupling for moving the two movable blades;

DETAILED DESCRIPTION OF THE PREFERRED EMBODIMENT

Figure 3A:
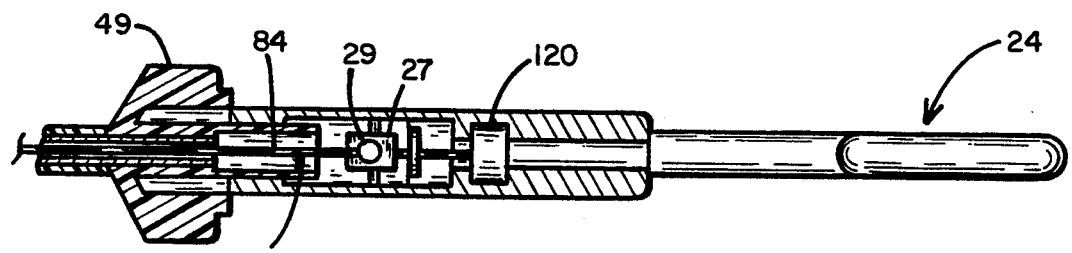
FIG. 3A is a partial top plan view of the proximal portion of FIG. 1.

Referring to FIG. 1, a bipolar electrosurgical scissors instrument 10 is shown for use in endoscopic or similar procedures. The instrument 10 has an elongated tubular member 12 of a diameter and length sufficient for use in cooperation with a procedure performed using a scope-type instrument. The tubular member 12 has a proximal end 14, a distal end 16 and a lumen 18 which extends for the entire length of the tubular member 12. As shown in the cross-sectional view of FIG. 2, the tubular member 12 comprises a metal tube 20 coated with an electrical insulator 22. The electrical insulator 22 is preferably a polymer such as Teflon ®. In addition to being an insulator, such a coating provides a lubricious surface which enhances its slidability through the lumen of an endoscope.

Disposed at the proximal end 14 of the tubular member 12 is a scissors-type handle assembly 24. The handle assembly 24 has a first handle member 26 having first and second ends, with the first end thereof having a bore 30 extending therethrough and wherein, at the distal portion thereof, the proximal end 14 of the tubular member 12 resides. The first handle member 26 does not pivot. At its second end the first handle member 26 has a loop 32 intended to receive the thumb of an operator.

The handle assembly 24 additionally has a second handle member 34 which is pivotal with respect to the first handle member 26 by being pivotally mounted to the first handle member 26 with a pivot pin 52. Pivotal movement is depicted by the arrow 21 shown in FIG. 1. The first end of the second handle member 34 has pivotally mounted thereto by pivot pin 23 an open top, U-shaped cradle member 27 in which is cradled a sphere 29 in direct communication with the distal blade members as described later. Situated at the second end of the handle member 34 is a loop 56 to receive the forefinger of the operator.

Press fit into the distal end 16 of the tubular member 12 is a blade assembly 58. As will be explained more fully later, the blade assembly 58 comprises a first blade member 60 and a second blade member 62 pivotally joined to each other by an insulated rivet or screw 64 which extends through bores formed through the two blade members 60, 62. Both blade members 60, 62 are pivotally movable with respect to each other.

With reference to FIGS. 1 and 2, it is seen that two rigid electrically conductive rods 66, 84, each preferably covered with a layer of electrical insulation, extend through the lumen 18 of the tubular member 12. Referring to FIGS. 1, 4, 5 and 6, which show the distal portion of the instrument 10, the rods 66, 84 are pivotally coupled to their respective blade members 60, 62 by respective rigid links 68, 69. The distal ends of the rods 66, 84 are turned laterally outwardly to fit through respective proximal pivot point openings 71, 73 of the links 68, 69 to thereafter form a rivet type connection. Situated at each of the proximal portions of the blade members 60, 62 in step-down sections thereof are laterally projecting posts 75, 77 which pass through distal pivot openings 78, 81 of the links 68, 69 to likewise form rivet type connections. The rigid links 68, 69 thereby can pivot at each of their respective proximal and distal end portions.

Figure 4:
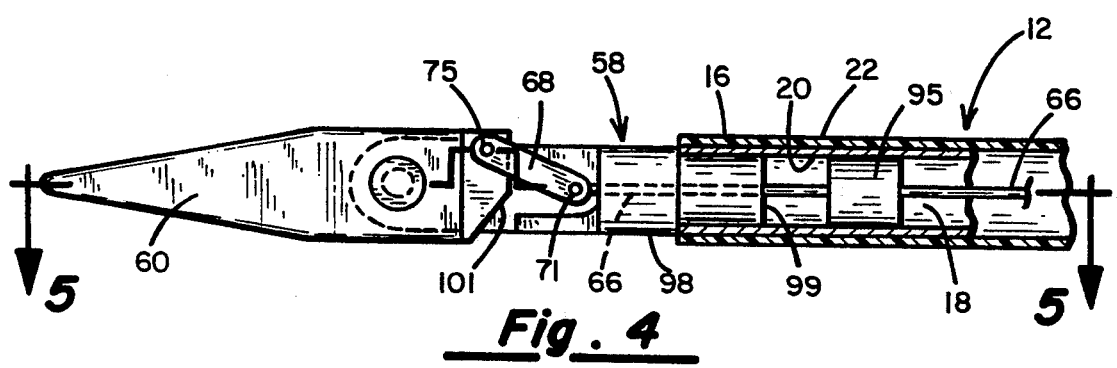
FIG. 4 is an enlarged side elevation view of the distal portion of FIG. 1.
Figure 5:
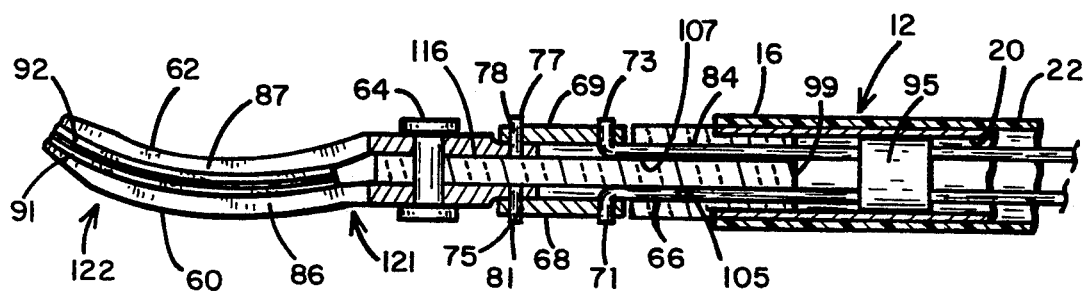
FIG. 5 is an enlarged top plan view of the distal portion of FIG. 1.

As is evident in FIGS. 4 and 5, the blade assembly 58 comprises, in addition to the blade members 60, 62, an insulated base 98 having a proximal portion 99 and a distal portion 101. The distal portion 101 has a bore 103 therethrough which provides a frame to which the blade members 60, 62 are pivotally attached via a pin or screw 64. The proximal portion 99 of the base 98 is press fit within the tubular member 12 and has two parallel longitudinal bores 105, 107 through which the rods 66, 84 pass. Proximal to the base 98 within the tubular member 12 is disposed and insulator member 95 through which the rods 66, 84 pass. This insulator member 95 functions to electrically isolate the rods 66, 84 from each other while mechanically acting to maintain them together. The respective proximal ends of the rods 66, 84 extend proximally from the proximal end of the tubular member 12 through the sphere 29 and terminate in a free wheeling electrical connector 120. The free wheeling connector 120 cannot move translationally in the handle assembly 24, but can freely rotate. External leads originating from an electrosurgical generator (not shown) as known in the art provide current to the connector 120 to thereby provide current to the rods 66, 84.

Because the sphere 29 is freely rotatable within the cradle member 27, the tubular member 12, and therefore the blade members 60, 62 can be rotatably moved. A knob 49 is therefore provided near the proximal end of the tubular member 12 to facilitate easy rotation by hand of the blade members 60, 62 when blade member positioning is performed by the operator. As seen in FIG. 1, the rotatable knob 49 is generally cylindrical in shape, having a bore 70 through its center along the central axis. The bore 70 is large enough to the tube 20 therein and allow the conductive rods 66, 84 to pass therethrough. The proximal end of the tube 20 is frictionally inserted into the bore 70, to thereby rotate when the knob 49 is rotated. The knob 49 has integrally formed tubular extension 45 which terminates in an annular flange 47. The handle assembly 24 has complimentarily shaped internal contours which the extension 45 and the flange 47 to thereby allow rotation thereof within the handle assembly 24. The knob 49 is preferably constructed of nylon so that the extension 45 and annular flange 47 will have lubricious characteristics for smoother rotation inside in the handle assembly 24. Because the rod 66, 84 are mechanically connected by the insulator member 95 which is stationary within the tube 20, rotation of the knob 49 results in rotation of the tube 20 as well as the rods 66, 84 to thereby also rotate the blade members 60, 62. Concurrently, the sphere 29 is rotated because the rods 66, 84 pass therethrough to their termination in the free wheeling electrical connector 120.

As is evident from FIG. 1, the operation of the handle assembly 24 by pivotally moving the second handle member 34 moves the cradle member 27 to thereby translationally move the sphere 29 which in turn moves both of the rods 66, 84 to thereby pivotally open and close the blade member 60, 62. In this manner, dual blade movement is accomplished. If only single blade movement is desired, the linkage arrangement described in co-pending and commonly assigned patent application Ser. No. 887,212, filed May 21, 1992, entitled "Surgical Scissors With Bipolar Coagulation Feature" and incorporated herein by reference, can be employed. In that arrangement only one blade is in the communication by moving the movable handle member of the handle assembly.

Referring to FIG. 5, each curved blade member 60, 62 includes a metal blank 86, 87 preferably stainless steel, to which is bonded on the inner scissors surfaces which interface each other respective electrical insulators such as a ceramic sheet or layer 92 of aluminum oxide or zirconia ceramic. Ceramic layers 91, 92 are each about 0.020 inch thick, and their working edges are honed at an angle of about 45 degrees, thereby creating a gap of about 0.040 inch wide between the leading interfacing surfaces when the blade member 60, 62 are closed. An RF current applied to the blade members 60, 62 can cauterize tissue, vessels and the like which bridge this gap. Copending and commonly assigned patent application Ser. No. 08/092,078, filed Jul. 16, 1993, and incorporated herein by reference details the procedure for manufacturing nonlinear blade members.

Figure 6:
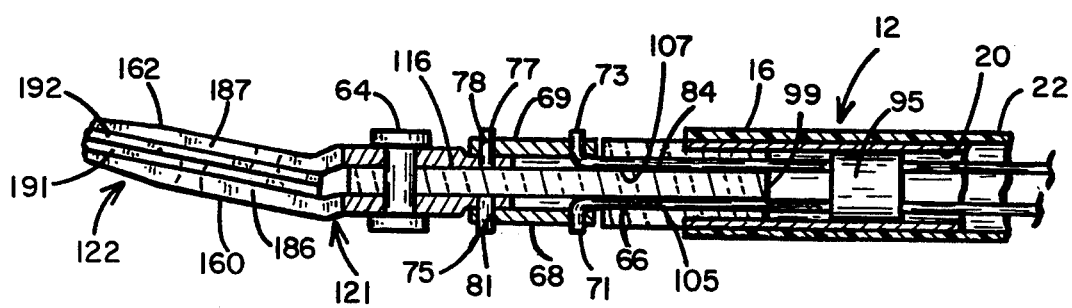
FIG. 6 is an enlarged top plan view of a second blade configuration.

FIG. 6 shows a second embodiment of blade members 160, 162 which are angled to thereby provide a non-parallel axis in relation to the axis immediately proximal to the blade members. As in the previously described embodiment, each blade member 160, 162 of the embodiment of FIG. 6 includes a metal blank 186, 187, preferably stainless steel, to which is bonded on the inner scissors surfaces respective electrical insulators such as a ceramic sheet or layer 191, 192 of aluminum oxide or zirconia. These layers 191, 192 are each about 0.020 inch thick, and their working edges are honed at an angle of about 45 degrees. In both embodiments, the respective blade members 60, 62 and 160, 162 are forced against each other by action of the tensile strength of the metal blanks thereof to thereby cause shearing action of interfacing honed edges of the respective ceramic layers 91, 92 and 191, 192 as the blades are pivoted.

In operation, the physician or other care provider directs the distal portion of the instrument of the present invention through the endoscope or other similar device to thereby position the blade members at the site of treatment. Thereafter, with current supplied to the blade members, the handle member is operated to cut tissue while simultaneously performing coagulation procedures.

While an illustrative and presently preferred embodiment of the invention has been described in detail herein, it is to be understood that the inventive concepts may be otherwise variously embodied and employed and the appended claims are intended to be construed to include such variations except insofar as claimed by the prior art.

I claim:

1. A bipolar electrosurgical scissors instrument comprising a proximal portion having a proximal linear axis and a distal blade portion affixed to said proximal portion and having cooperating first and second parallel cutting blade members wherein at least one cutting blade member is pivotable relative to said proximal portion and wherein the cutting blade members have a non-parallel axis in relation to the proximal linear axis, said cutting blade members each comprising an electrically conductive outer surface and an electrically non-conductive inner surface, said inner surface comprising a ceramic layer having a honed cutting edge whereby pivoting of the at least one cutting blade member causes the honed cutting edge of the first cutting blade member to wipe the honed cutting edge of the second cutting blade member and handle means affixed to said proximal portion and operatively coupled to said at least one cutting blade member for imparting pivoting motion to said at least one cutting blade member.

2. A bipolar electrosurgical scissors instrument as claimed in claim 1 wherein the electrically conductive outer surface of each cutting blade member is a metal.

3. A bipolar electrosurgical scissors instrument as claimed in claim 2 wherein the metal is stainless steel.

4. A bipolar electrosurgical scissors instrument as claimed in claim 1 wherein the cutting blade members are curved in relation to the proximal linear axis.

5. A bipolar electrosurgical scissors instrument as claimed in claim 1 wherein the cutting blade members are angled in relation to the proximal linear axis.

6. A bipolar electrosurgical scissors instrument as claimed in claim 1 wherein the cutting blade members are rotatable.

7. A bipolar electrosurgical scissors instrument comprising:
   (a) an elongated tubular member having a proximal end, a distal end, and a lumen extending therebetween, said tubular member having a proximal linear axis;
   (b) a cutting blade portion disposed at the distal end of the tubular member, said cutting blade portion having first and second parallel blade members wherein at least one blade member is pivotable and wherein the blade members have a non-parallel axis in relation to the linear axis of the tubular member, said blade members each comprising an electrically conductive outer surface and an electrically non-conductive inner surface, said inner surface comprising a ceramic layer having a honed cutting edge whereby pivoting of the at least one blade member causes the honed cutting edge of the first blade member to wipe the honed cutting edge of the second blade member; and
   (c) a handle disposed at the proximal end of the tubular member, said handle being in communication with the blade members and being hand operable to thereby produce pivotal action of the at least one blade member.

8. A bipolar electrosurgical scissors instrument as claimed in claim 7 wherein the electrically conductive outer surface of each blade member is a metal.

9. A bipolar electrosurgical scissors instrument as claimed in claim 8 wherein the metal is stainless steel.

10. A bipolar electrosurgical scissors instrument as claimed in claim 7 wherein the blade members are curved in relation to the proximal linear axis.

11. A bipolar electrosurgical scissors instrument as claimed in claim 7 wherein the blade members are angled in relation to the proximal linear axis.

12. A bipolar electrosurgical scissors instrument as claimed in claim 7 wherein the blade members are rotatable.

* * * * *